United States Patent [19]

Parsons

[11] Patent Number: 4,682,609
[45] Date of Patent: Jul. 28, 1987

[54] CERVICAL-DILATION METER

[76] Inventor: Natan Parsons, 71 Babcock St., Brookline, Mass. 02146

[21] Appl. No.: 801,640

[22] Filed: Nov. 25, 1985

[51] Int. Cl.⁴ .............................................. A61B 5/10
[52] U.S. Cl. .................................... 128/775; 128/778; 33/512
[58] Field of Search ............... 128/774, 775, 778, 361; 33/511, 512, 143 C, 149 R

[56] References Cited

U.S. PATENT DOCUMENTS 2,575,343  7/1948  Heiman .................................. 33/512
4,207,902  6/1980  Krementsov ........................ 128/775

Primary Examiner—Kyle L. Howell
Assistant Examiner—Randy Citrin
Attorney, Agent, or Firm—Cesari and McKenna

[57] ABSTRACT

A meter (10) for measuring cervical dilation during labor includes rings (20 and 22) that fit at the bases of the user's fingers (24 and 26). Pivot arms (14 and 16) mount the rings (20 and 22) at one end and a scale and indicator (30) at the other end. Scale indicia indicate the separation of the rings. Ring separation can be translated into the separation of the finger tips and thus into cervical dilation.

6 Claims, 9 Drawing Figures

|        | 5 | 10 | 15 | 20 | 25 | 30 | 35 | 40 |
|--------|---|----|----|----|----|----|----|----|
| RED    |   |    |    |    |    |    |    |    |
| BLUE   |   |    |    |    |    |    |    |    |
| GREEN  |   |    |    |    |    |    |    |    |
| YELLOW |   |    |    |    |    |    |    |    |

FIGURE 5

CERVICAL-DILATION METER

BACKGROUND OF THE INVENTION

The present invention is directed to devices for measuring cervical dilation.

In the early stages of labor, the doctor monitors cervical dilation to determine how far labor has advanced. Dilation monitoring is typically performed by inserting two fingers and noting how far they can be extended laterally.

Needless to say, this type of measurement is far from repeatable. Even if a given doctor comes to recognize different degrees of dilation by feel, he cannot reliably communicate that degree of dilation to another doctor without some objective scale. To overcome this shortcoming—i.e., to provide a way to assess dilation by means of an objective scale—devices for measuring cervical dilation have been proposed, but they have not attracted widespread use. The reason seems to be that the patient finds insertion of foreign objects more objectionable than insertion of the doctor's fingers.

It is accordingly an object of the present invention to permit an objective dilation measurement without the objectionable insertion of foreign objects.

SUMMARY OF THE INVENTION

The foregoing and related objects are achieved through the use of a dilation meter that comprises a pair of pivot arms pivotably mounted to each other. On one end of each arm is a ring adapted to fit around the bases of two adjacent fingers of a doctor. On the other end of one arm is a scale on which are provided indicia indicating meter pivot angle, while an indicating element such as a pointer is on the other end of the other arm to point to indicia on the scale. The scale is positioned with respect to the rings so that it fits in the palm of the doctor's hand when the rings are on the bases, rather than on the tips, of his fingers.

Dilation is determined from the angle measurement by means of a function, keyed to the sizes (lengths and thicknesses) of the doctor's fingers, that converts pivot angle to dilation. The doctor makes an initial determination of the size range for his fingers to determine which of several such conversion functions to use. The function may be provided on a separate table, or multiple functions may be provided on the device itself, and the functions are based on placement of the rings at the bases of the doctor's fingers rather than at their tips. In this way, an objective, repeatable dilation determination can be made without the need to have the meter touch the patient.

BRIEF DESCRIPTION OF THE DRAWINGS

These and further features and advantages are described in connection with the accompanying drawings, in which:

FIG. 5 is a detailed view of the table provided on the container of FIG. 3;

FIG. 10 is a front elevational view of another alternate embodiment of the meter of the present invention.

DETAILED DESCRIPTION OF THE PREFERRED EMBODIMENTS

Figure 1:
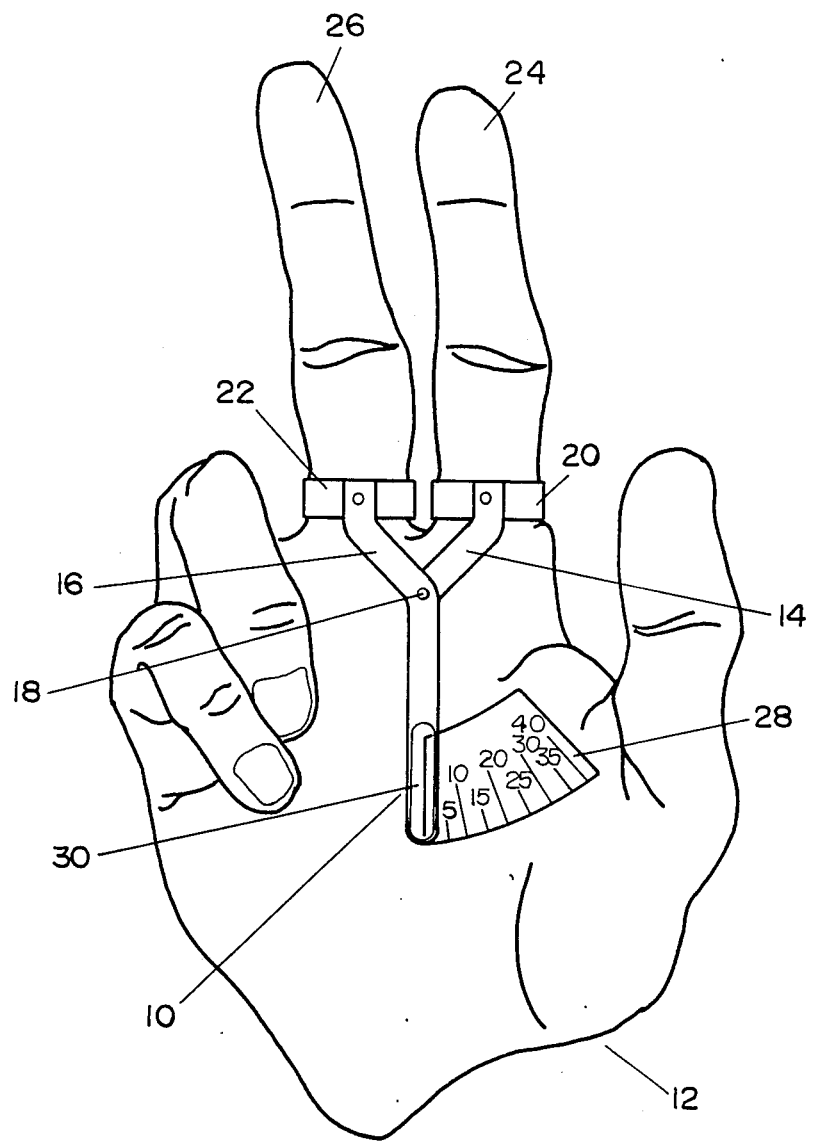
FIG. 1 is a front elevational view of the dilation meter of the present invention shown in position on the doctor's fingers.

FIG. 1 shows a dilation meter 10 of the present invention in place on a doctor's hand 12. It includes two pivot arms 14 and 16 mounted together for pivoting about a pivot axis 18. At the distal ends of the arms 14 and 16 are mounted two rings 20 and 22, respectively. Rings 20 and 22 are adjustable in diameter and enclose the bases of the two adjacent fingers 24 and 26 that the doctor uses to perform the dilation measurement. At the proximal end of one pivot arm 14 is a scale 28 on which indicia are inscribed at different angular positions. At the proximal end of the other pivot arm 16 is an indicating element in the form of an elongated extension with a window 30 through which the doctor can see an indicium and thereby note the pivot angle—typically in arbitrary units—when his fingers are at their maximum lateral extension in the cervix. All parts of the meter are made of a plastic that will not be adversely affected by irradiation or other ordinary sterilization procedures.

Figure 2:
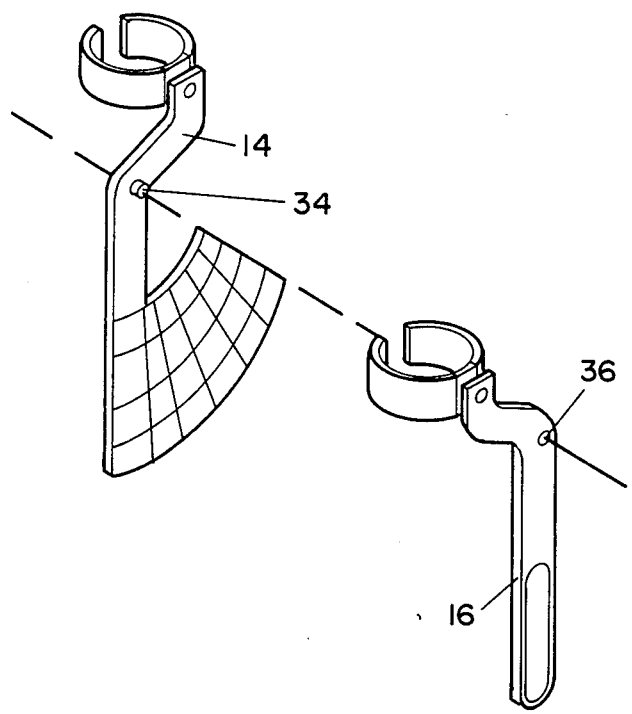
FIG. 2 is an exploded view of the meter of FIG. 1.

As FIG. 2 shows, arm 14 is snap fit to arm 16. A resilient flanged boss 34 provided on arm 14 at its pivot axis extends through a registering aperture 36 at the pivot axis of arm 16 and thereby holds the two arms together.

Since the dilation for a given meter angle depends on the size of the doctor's fingers, the box 38 (FIGS. 3 and 4) in which the meters are delivered is provided with a calibration device. Perforations on the side of the box 38 define a tab 39 whose removal reveals an opening 40 in which a slide 42 is slidably mounted by any appropriate means such as track-defining internal rails 44 and 46 secured by spacers 48 and 50 to one wall 52 of the box 38. Complementary edges 54 and 56 on the wall and the slide define the opening 40, so the size of the opening 40 varies with the position of the slide 42.

Length indicia 54 are printed on the box wall 52 adjacent the slide 42, and a pointing indicium 57 is printed on the slide 42 to point to them. The size indicia in the illustrated embodiment are different colors, say, red, blue, green, and yellow.

Figure 3:
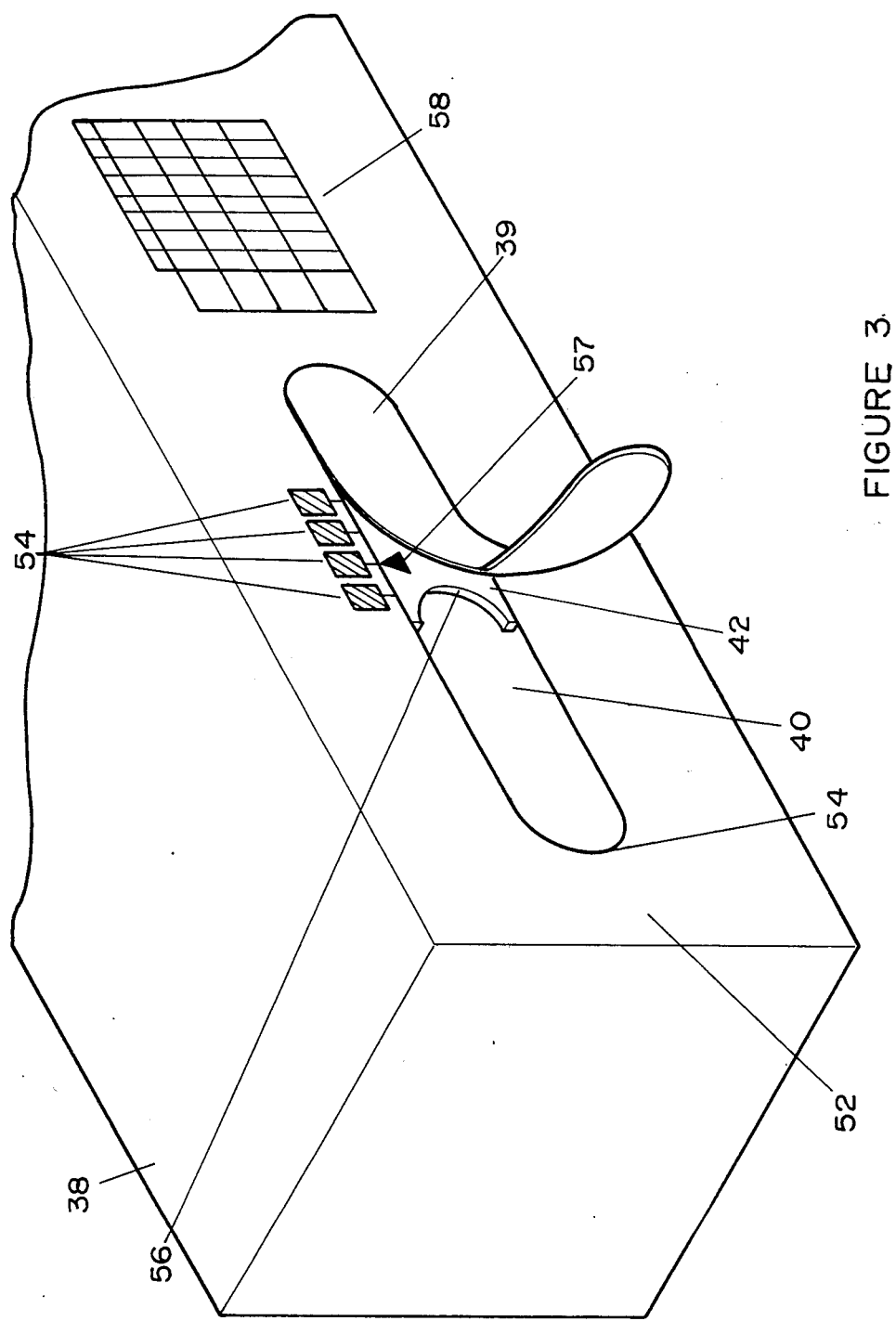
FIG. 3 is an isometric view of a container for dilation meters of the type shown in FIG. 1.
Figure 4:
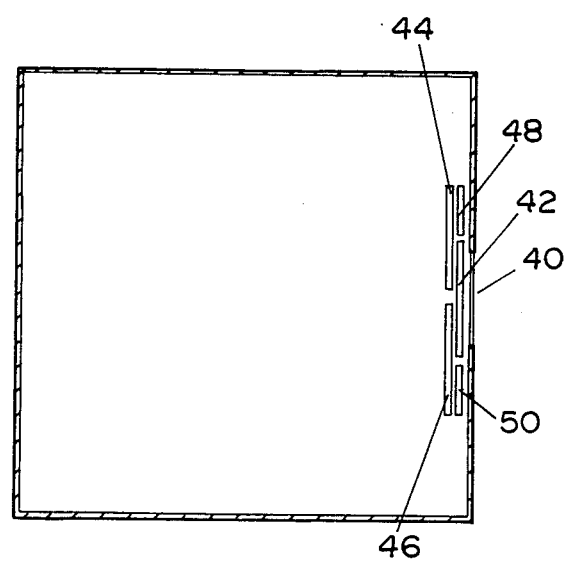
FIG. 4 is a cross-sectional view of a part of the container of FIG. 3.

Before a doctor uses a meter for the first time, he fits the rings 20 and 22 on the bases of his fingers and places his fingers in the opening 40 with the slide 42 disposed in a position somewhat to the left in FIG. 3. He opens his fingers until the meter reaches a predetermined reading, sliding the slide to the right as he does so. He then observes the size indicium 54 to which the pointing indicium 56 points when the meter reaches the predetermined reading, and this is an indication of the relative size of his fingers. Best calibration is obtained when the doctor's fingers are crooked in the manner in which they are crooked when he takes a dilation measurement.

When the doctor then uses the meter 10 to take an actual dilation measurement, he notes the angle indicium on the meter and consults a table 58 on container wall 52 to find the entry under the angle reading for his color. This is the dilation measurement. FIG. 5 shows the table in detail.

In practice, the doctor may rely for his own purposes on the angle measurement alone, converting to the dilation measurement only in communicating his measurements to others.

Figure 6:
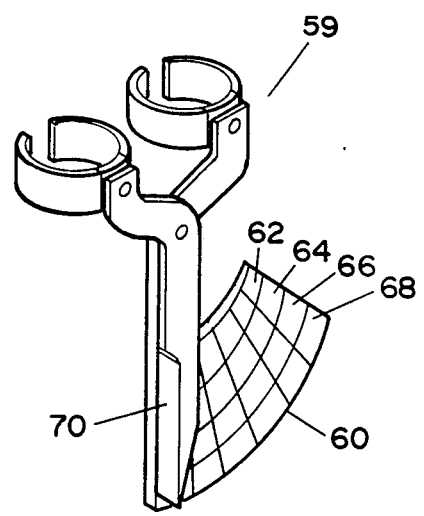
FIG. 6 is a perspective view of an alternate embodiment of the meter of the present invention.

To avoid the need to consult a table on a separate box to determine dilation, the dilation-meter scale may be arranged to provide a dilation reading directly. Such a meter 59 is depicted in FIG. 6. The scale 60 on meter 59 provides indicia in four parallel ranges 62, 64, 66, and 68. Each range corresponds to a different finger size, and the doctor makes the dilation measurement by simply observing the indicium pointed to by the indicating element, in this case, a pointer 70.

Figure 7:
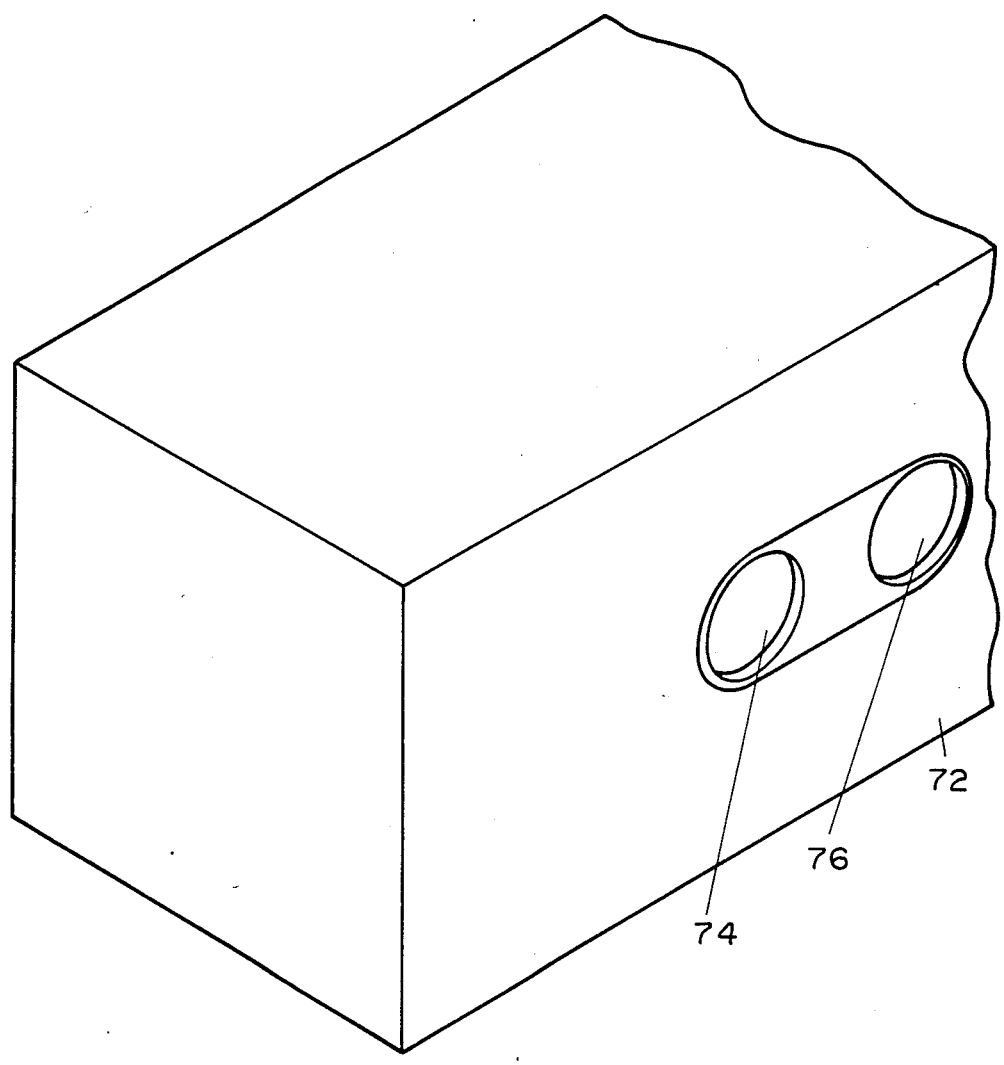
FIG. 7 is an isometric view of an alternate embodiment of the container.

The meter 59 shown in FIG. 6 may come in a container like box 72 of FIG. 7. Removal of a tab (not shown) reveals two holes 74 and 76 representing a predetermined cervical dilation. The initial calibration for the type of meter shown in FIG. 6 is performed by placing the tips of the doctor's fingers in the two holes and observing the range in which the pointer 70 points to an indicium representing the predetermined dilation.

Figure 8:
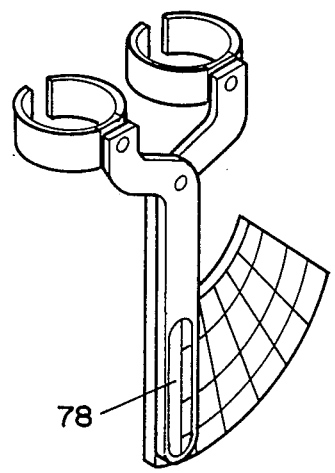
FIG. 8 is an isometric view of another alternate embodiment of the meter of the present invention.

FIG. 8 depicts a meter in which the indicating element includes a magnifying "glass" 78, typically made of transparent plastic, that magnifies the images of the indicia so that the doctor can read them more easily.

Figure 9:
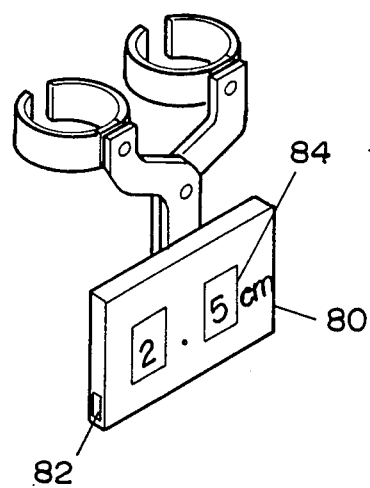
FIG. 9 is an isometric view of another alternate embodiment of the meter of the present invention.

To further simplify the dilation determination, the disposable part of the meter can be provided without an integral scale. Instead, it could be adapted to be mechanically attached to a position encoder included in an electronic scale 80 (FIG. 9). With this type of an arrangement, the doctor simply presses a button when his fingers are in holes 74 and 76. The scale 80 is thereby automatically calibrated and displays dilation on an LCD display 84.

To increase measurement resolution in a strictly mechanical embodiment of the present invention, angle-multiplying arrangements can be used. An example is illustrated in FIG. 10, which shows rings 20 and 22 on arms 14 and 16 that are pivotably secured to each other for pivoting about a pivot axis 18. Instead of being attached directly to a pointer and scale, however, the arms 14 and 16 in the FIG. 10 embodiment are pivotably secured to auxiliary, angle-multiplying arms 86 and 88, respectively, for pivoting with respect to them about pivot points 90 and 92. The auxiliary arms 86 and 88 are in turn pivotably secured to each other at pivot point 94. A scale 98 and indicating element 98 are provided on the ends of auxiliary arms 86 and 88, respectively, and it becomes apparent upon reflection that a small change in the angle between the main arms 14 and 16 results in a much larger change in the angle between the auxiliary arms 86 and 88. The FIG. 10 embodiment thus affords greater resolution in the dilation measurement.

In light of the foregoing description, it can be appreciated that the present invention can be practiced in a wide variety of embodiments. It permits a doctor to make an objective dilation measurement without touching the patient with an objectional foreign object. The present invention therefore constitutes a significant advance in the art.

What is claimed as new and desired to be secured by Letters Patent of the United States is:

1. For measuring the cervical dilation during the initial stages of labor, a dilation meter comprising:
   A. first and second pivot arms pivotably mounted to each other for pivoting with respect to each other about a common pivot axis extending through pivot points on the pivot arms;
   B. first and second rings provided on the first and second pivot arms, respectively, and spaced from the pivot points on the respective pivot arms, the rings being adapted to fit simultaneously on the bases of adjacent fingers of a user; and
   C. calibrated measurement means for providing a quantitative indication of the lateral extension of the tips of fingers whose bases are positioned in the rings, the measurement means comprising:
      i. a scale on the first pivot arm having a plurality of spaced scale indicia indicating different degrees of cervical dilation, and
      ii. an indicator positioned with respect to the scale to indicate the indicium that indicates the cervical dilation that corresponds to the lateral extension of the tips of the fingers whose bases are positioned in the rings.

2. A dilation meter as defined in claim 1 wherein the scale indicia include a plurality of sets of spaced scale indicia, the different sets being associated with different finger sizes, and wherein the indicator indicates different scale indicia in each set thereof when the pivot arms form different angles with respect to each other, the scale indicia indicated by the indicator in each set representing the lateral extensing of fingers of the sizes associated with that set.

3. A dilation meter as defined in claim 1 wherein the indicator is a pointer that points to the scale indicia.

4. A dilation meter as defined in claim 1 wherein the rings are expandable to accommodate fingers of different diameters.

5. A dilation meter as defined in claim 1 wherein the pivot points are aligned between the rings and measurement means on the pivot arms and the measurement means are located on ends of the pivot arms opposite said rings.

6. For measuring cervical dilation during the initial stages of labor, a method comprising the steps of:
   A. providing a dilation meter that includes a pair of rings, adapted to fit simultaneously on the bases of adjacent fingers of a user, and measurement means connected to the rings for providing an indication of the lateral extension of the tips of fingers whose bases are positioned in the rings;
   B. placing the rings around the bases of the user's fingers;
   C. extending the two fingers of the user to opposite edges of a patient's cervix; and
   D. observing the indication provided by the measurement means, thereby taking a measurement of the patient's cervical dilation.

* * * * *